United States Patent
Kim (10) Patent No.: US 9,625,381 B2
(45) Date of Patent: *Apr. 18, 2017

(54) SENSOR INCLUDING NANOSTRUCTURE AND METHOD FOR FABRICATING THE SAME

(71) Applicant: SK INNOVATION CO., LTD., Seoul (KR)

(72) Inventor: Jun-Hyung Kim, Daejeon (KR)

(73) Assignee: SK INNOVATION CO., LTD., Seoul (KR)

( * ) Notice: Subject to any disclaimer, the term of this patent is extended or adjusted under 35 U.S.C. 154(b) by 87 days.

This patent is subject to a terminal disclaimer.

(21) Appl. No.: 14/554,856

(22) Filed: Nov. 26, 2014

(65) Prior Publication Data
US 2015/0177138 A1    Jun. 25, 2015

(30) Foreign Application Priority Data
Dec. 19, 2013  (KR) .................. 10-2013-0159753

(51) Int. Cl.
*G01N 21/55* (2014.01)
*G01N 21/552* (2014.01)
*G01N 33/543* (2006.01)
*B32B 37/24* (2006.01)
*B32B 38/00* (2006.01)
*C23C 16/455* (2006.01)

(52) U.S. Cl.
CPC .......... *G01N 21/554* (2013.01); *B32B 37/24* (2013.01); *B32B 38/0008* (2013.01); *C23C 16/45525* (2013.01); *G01N 33/54346* (2013.01); *B32B 2037/243* (2013.01); *Y10T 156/10* (2015.01)

(58) Field of Classification Search
CPC .... G01N 21/553; G01N 21/55; G01N 21/554; G01N 21/474; G01N 21/57
USPC ......................................................... 356/445
See application file for complete search history.

(56) References Cited

U.S. PATENT DOCUMENTS

| | | | | |
|---|---|---|---|---|
| 7,220,482 | B2 * | 5/2007 | Mino | B05D 1/185 257/E29.129 |
| 8,414,926 | B1 | 4/2013 | Turos et al. | |
| 2004/0203256 | A1 | 10/2004 | Yang et al. | |
| 2007/0194694 | A1 * | 8/2007 | Reddy | B82Y 20/00 313/503 |
| 2009/0294803 | A1 * | 12/2009 | Nuzzo | B82Y 10/00 257/213 |

(Continued)

OTHER PUBLICATIONS

Steichen, S., et al., A review of current nanoparticle and targeting moieties for the delivery of cancer therapeutics, European Journal of Pharmaceutical Sciences, Dec. 20, 2012, pp. 416-427, vol. 48, No. 3.

(Continued)

*Primary Examiner* — Tarifur Chowdhury
*Assistant Examiner* — Md M Rahman
(74) *Attorney, Agent, or Firm* — I P & T Group LLP (57) ABSTRACT

Provided is a sensor having a nanostructure as a sensing element and a fabrication method thereof. The sensor includes a nanostructure as a sensing element for sensing a marker over a substrate, wherein the nanostructure includes: a linker layer, including linkers, bonded to the substrate; and metallic nanoparticles grown from metal ions bonded to the linkers.

34 Claims, 5 Drawing Sheets (56) References Cited

U.S. PATENT DOCUMENTS

| | | | | |
|---|---|---|---|---|
| 2010/0155310 A1* | 6/2010 | Enomura | ............. | B01F 3/0807 |
| | | | | 209/668 |
| 2010/0178481 A1* | 7/2010 | George | ................ | C23C 16/402 |
| | | | | 428/213 |
| 2012/0282721 A1* | 11/2012 | Liao | ....................... | C09D 11/52 |
| | | | | 438/72 |
| 2013/0242297 A1* | 9/2013 | Thoniyot | ............... | B82Y 30/00 |
| | | | | 356/244 |
| 2013/0327392 A1 | 12/2013 | Weitekamp et al. | | |
| 2014/0054788 A1* | 2/2014 | Majima | ................. | B82Y 10/00 |
| | | | | 257/773 |
| 2014/0110608 A1* | 4/2014 | Kim | ..................... | B82B 3/0023 |
| | | | | 250/492.3 |
| 2015/0027755 A1* | 1/2015 | Tsujimoto | ............. | B82Y 30/00 |
| | | | | 174/253 |

OTHER PUBLICATIONS

Extended European Search Report issued by the European Patent Office on May 6, 2015.
Office Action issued by the European Patent Office on Jan. 12, 2017.

* cited by examiner

SENSOR INCLUDING NANOSTRUCTURE AND METHOD FOR FABRICATING THE SAME

CROSS-REFERENCE TO RELATED APPLICATIONS

The present application claims priority of Korean Patent Application No. 10-2013-0159753, filed on Dec. 19, 2013, which is incorporated herein by reference in its entirety.

BACKGROUND

1. Field

Various embodiments of the present disclosure relate to a sensor having a nanostructure as a sensing element, and a fabrication method thereof.

2. Description of the Related Art

Nanostructures are widely used for sensors that sense light, enzymes, viruses, gases, and heavy metals by ligandizing a metallic nanoparticle.

Particularly, in nanoparticles made of gold, a noble metal, a Surface Plasmon Resonance (SPR) phenomenon occurs. The SPR phenomenon occurs when a collective oscillation of electrons is stimulated by incident light. Gold nanoparticles have desirable physical, chemical, and optical properties to support this phenomenon and its applications.

For example, biosensors often include nanostructures for electrically connecting an anode and a cathode, and the nanostructures include nanoparticles that are combined with or coated with a receptor.

Since nanostructure's electrical conductivity varies according to the wavelength of absorbed light, this nanostructure technology may be applied to optical sensors.

Nanostructures may be fabricated in diverse sizes to suit the particular application field and may be used for highly sensitive electrical, chemical, and optical sensing. However, since the process is complicated, there is limited ability to apply the technology in mass-production. Moreover, nanoparticles need to be prepared uniformly and with high density for electrical sensing and high-speed operation.

SUMMARY

Various embodiments are directed to a sensor including a nanostructure, and a method for fabricating the nanostructure that allows for mass-production that is simple and suitable for controlling nanoparticle size.

Also, various embodiments are directed to a sensor including a nanostructure that can secure operation stability, reproducibility, and reliability in an application device, even when scaled.

In an embodiment, a sensor includes a nanostructure as a sensing element for sensing a marker over a substrate, wherein the nanostructure includes: a linker layer including linkers bonded to the substrate; and metallic nanoparticles formed over the linker layer by the metal ions.

The sensor may further include: receptors bonded to the surface of the metallic nanoparticles.

The receptors may be one or more selected from an enzyme substrate, a ligand, an amino acid, a peptide, a protein, a nucleic acid, a lipid, and carbohydrates.

The substrate may include a surface layer to which the linkers are bonded.

The fabrication of the nanostructure may further include an organic surfactant of one or more kinds bonded to surfaces of the metal ions before the metal ions are grown, or surfaces of the nanoparticles/metal ions which are being grown.

The metallic nanoparticles may have an average particle diameter of about 0.5 nm to 3.0 nm.

Each of the linkers may include one functional group selected from an amine group, a carboxyl group, and a thiol group, that are suitable for bonding to the metal ions.

The linker layer may include a self-assembled monomolecular layer (a layer of particles one molecule thick) or a silane compound layer.

The metallic nanoparticles may be arranged separately from each other to form a single layer (a layer of one metallic nanoparticle in thickness).

The nanostructure may have a vertical multi-stack structure where the linker layer and the nanoparticle layer are stacked alternately and repeatedly.

In another embodiment, a sensor may include a nanostructure as a sensing element for sensing a marker over a substrate, wherein the nanostructure includes: dielectric material particle supporters formed over the substrate; linkers bonded to a surface of the dielectric material particle supporters; and metallic nanoparticles grown from metal ions bonded to the linkers.

The sensor may further include receptors bonded to surfaces of the metallic nanoparticles.

The receptors may be one or more selected from an enzyme substrate, a ligand, an amino acid, a peptide, a protein, a nucleic acid, a lipid, and carbohydrates.

Dielectric material particle supporters with the linkers bonded thereto may be arranged over the substrate to form a single supporter layer or a vertically stacked multi-layer.

Each of the linkers may include one functional group selected from an amine group, a carboxyl group, and a thiol group that are suitable for bonding to the metal ions.

The nanostructure may further include an organic surfactant of one or more kinds that are bonded to surfaces of the metal ions before the metal ions are grown or while the metal ions are being grown.

The metallic nanoparticles may have an average particle diameter of about 0.5 nm to 3.0 nm.

In another embodiment, a method for fabricating a sensor includes: forming a linker layer including linkers over a substrate; bonding metal ions to the linkers of the linker layer; forming metallic nanoparticles by growing the metal ions; and bonding receptors to surfaces of the metallic nanoparticles.

The metal ions may be grown by application of energy.

The method may further include supplying an organic surfactant of one or more kinds before or during the application of the energy.

The linker layer may be formed by applying a linker solution in which the linkers are dissolved in a solvent to a surface of the substrate.

The linker layer may be formed through an Atomic Layer Deposition (ALD) method using a gas containing the linkers.

Each of the linkers may have a functional group suitable for bonding to the metal ions.

The bonding of the metal ions to the linkers of the linker layer may include applying a metal precursor to the linkers.

The bonding of the metal ions to the linkers of the linker layer may include applying a metal precursor solution where the metal precursor is dissolved to the linkers, or supplying a metal precursor gas to the linkers.

The energy may be one or more selected from heat energy, chemical energy, light energy, vibration energy, ion beam energy, electron beam energy, and radiation energy.

The metallic nanoparticles may be formed of one or more selected from metal nanoparticles, metal oxide nanoparticles, metal nitride nanoparticles, metal carbide nanoparticles, and intermetallic compound nanoparticles, by supplying a different kind of material than the metal ions during the application of the energy.

In another embodiment, a method for fabricating a sensor may include forming dielectric material particle supporters with linkers bonded thereto over a substrate; bonding metal ions to the linkers; forming metallic nanoparticles out of the metal ions; and bonding receptors to surfaces of the metallic nanoparticles.

The metal ions may be grown by application of energy. The method may further include supplying an organic surfactant of one or more kinds before or during the application of the energy.

The forming of dielectric material particle supporters with the linkers bonded thereto may include: preparing a supporter material by mixing dielectric material particle supporters and linkers in a solvent to form a solution; and coating the substrate with the supporter material or depositing the supporter material on the substrate via the dielectric material supporter/linker solution.

The bonding of the metal ions to the linkers may include applying a metal precursor to the linkers.

The bonding of the metal ions to the linkers may include applying a solution containing the metal precursors to the linkers, or supplying a metal precursor gas to the linkers.

The energy may be one or more selected from heat energy, chemical energy, light energy, vibration energy, ion beam energy, electron beam energy, and radiation energy.

The metallic nanoparticles may be formed of one or more selected from the group consisting of metal nanoparticles, metal oxide nanoparticles, metal nitride nanoparticles, metal carbide nanoparticles, and intermetallic compound nanoparticles, by supplying a different kind of material than the metal ions during the application of energy.

DETAILED DESCRIPTION

Hereinafter, a sensing element and a fabrication method thereof according to embodiments of the present disclosure will be described in detail with reference to the accompanying drawings. The present disclosure may, however, be embodied in different forms and should not be construed as limited to the embodiments set forth herein. Rather, these embodiments are provided so that this disclosure will be thorough and complete, and will fully convey the scope of the present disclosure to those skilled in the art. In addition, the drawings are not necessarily to scale and, in some instances, proportions may have been exaggerated in order to clearly illustrate features of the embodiments. Throughout the disclosure, reference numerals correspond directly to the like numbered parts in the various figures and embodiments. Also, all "embodiments" mentioned refer to embodiments of the present disclosure.

It should be readily understood that the meaning of "on" and "over" in the present disclosure should be interpreted in the broadest manner such that "on" means not only "directly on" but also "on" something with an intermediate feature(s) or a layer(s) therebetween, and that "over" means not only directly over but also over something with an intermediate feature(s) or a layer(s) therebetween. It is also noted that in this specification, "connected/coupled" refers to one component not only directly coupling another component but also indirectly coupling another component through an intermediate component. In addition, a singular form may include a plural form, and vice versa, as long as it is not specifically mentioned.

Unless otherwise mentioned, all terms used herein, including technical or scientific terms, have the same meanings as understood by those skilled in the technical field to which the present disclosure pertains. In this specification, a detailed description of known functions and configurations will be omitted when it may obscure the subject matter of the present disclosure.

Figure 1:
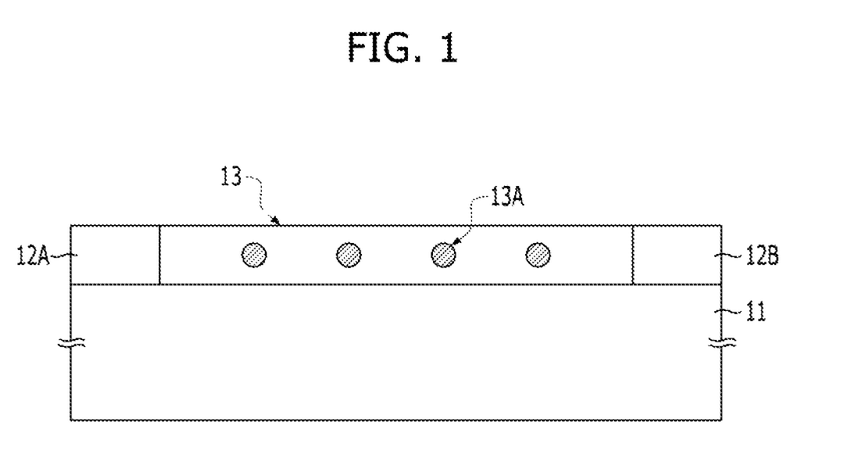
FIG. 1 is a cross-sectional view showing a portion of a sensor in accordance with a first embodiment.

FIG. 1 is a cross-sectional view showing a portion of a sensor platform in accordance with a first embodiment.

Referring to FIG. 1, an anode 12A and a cathode 12B are formed over a substrate 11 to confront each other. Also, a nanostructure 13 is formed over the substrate 11. The shape and material of the substrate 11 may be different according to the application field. The nanostructure 13 may include metallic nanoparticles 13A in a single layer (a layer one metallic nanoparticle thick) or in multiple layers (a layer of multiple metallic nanoparticles in thickness).

FIG. 1 shows a portion of a sensor that is an embodiment. However, the technology of the present disclosure may be applied to diverse three-dimensional structures and the position and shape of the nanostructure 13 may be different to suit the applied platform. The present invention may be applied whenever a sensor having metallic nanoparticles is used to sense a marker. A marker is a target material or form of energy. Examples of markers include light, enzymes, viruses, gases, and heavy metals. The nanostructure 13 of the present invention may be applied in various physical structures using a variety of materials.

Sensor Platform and Fabrication Method Thereof in Accordance with a First Embodiment of the Present Invention FIGS. 2A to 2E are cross-sectional views illustrating a method for fabricating a sensor platform in accordance with a first embodiment. This embodiment focuses on fabrication of the nanostructure, which is a sensing element. The method for fabricating a sensor platform in accordance with the first embodiment includes: bonding linkers 120A to a substrate 110 (see FIG. 2A); bonding metal ions 130 to the linkers 120A (see FIGS. 2B and 2C); and forming metallic nanoparticles 140 out of metal ions 130 by applying energy to the metal ions 130 (see FIG. 2D).

Figure 2A:
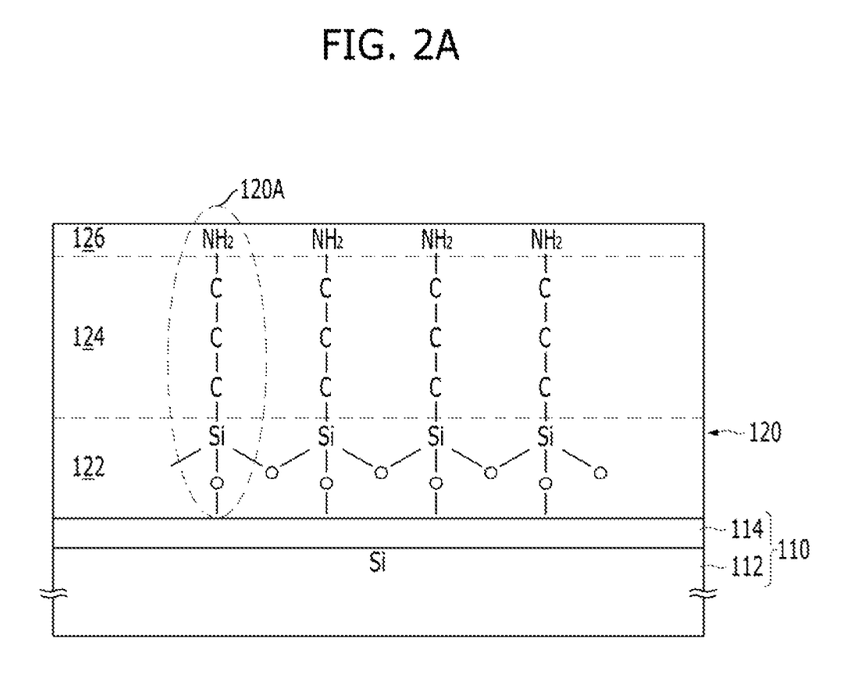
FIGS. 2A to 2E are cross-sectional views illustrating a method for fabricating a sensor platform in accordance with a first embodiment.

The method for fabricating a sensor platform in accordance with the first embodiment may further include bonding a receptor 150 on the surface of the metallic nanoparticles 140. Also, the method may further include supplying an organic surfactant of one or more kinds to control the size of the metallic nanoparticles 140, before or during the application of energy. FIG. 2A shows the linkers 120A bonded to the prepared substrate 110. The substrate 110 may have a surface layer 114 having a functional group suitable for bonding to the linkers 120A. For example, the substrate 110 may be a silicon substrate 112 having a silicon oxide ($SiO_2$) layer as the surface layer 114.

The substrate 110 may be a semiconductor substrate, a transparent substrate, or a flexible substrate, and the material, structure and shape of the substrate 110 may be different depending on the application device to which it is applied. Also, the substrate 110 may serve as a physical support to the constituent elements of the sensor platform, e.g., an electrode, or the substrate 110 may be a raw material of the constituent elements.

Non-limiting examples of the flexible substrate include a flexible polymer substrate formed of polyethylene terephthalate (PET), polyethylene naphthalate (PEN), polyimide (PI), polycarbonate (PC), polypropylene (PP), triacetyl cellulose (TAC), polyethersulfone (PES), polydimethylsiloxane (PDMS), or a mixture thereof. When a flexible substrate is used, the surface layer 114 of the substrate may be made of an organic material having a functional group (e.g., —OH functional group) capable of being bonded to the linkers.

The surface layer 114 of the substrate 110 may also be a metal thin film. The metal thin film may have a thickness of about 100 nm or less. According to an embodiment, the metal thin film may have a thickness of about 1 nm to 100 nm. When the metal thin film is extremely thin, about 1 nm or less, the uniformity of the thin film may deteriorate. Non-limiting examples of the material for the metal thin film, which is used as the surface layer 114 may include transition metals, noble metals, metals, and mixtures thereof. Examples of the transition metals include Sc, Y, La, Ac, Ti, Zr, Hf, V, Nb, Ta, Cr, Mo, W, Mn, Te, Re, Fe, Ru, Os, Co, Rh, Ir, Ni, Pd, Pt, Cu, Ag, Au, and mixtures thereof, and examples of the metals include Li, Na, K, Rb, Cs, Fr, Be, Mg, Ca, Sr, Ba, Ra, Zn, Cd, Al, Ga, In, Tl, Ge, Sn, Pb, Sb, Bi, Po, and mixtures thereof.

A linker layer 120 may be formed over the substrate 110 and may be composed of linkers 120A. The linker layer 120 may be a self-assembled monomolecular layer bonded to the surface of the substrate 110.

The linkers 120A may be organic linkers that are chemically bonded to or adsorbed on the surface of the substrate 110 and may be chemically bonded with metal ions. To be specific, the linkers 120A may be organic linkers having both a functional group 122 that is chemically bonded to or adsorbed on the surface layer 114 of the substrate and a functional group 126 that is chemically bonded to metal ions (to be formed later). The chemical bond may include a covalent bond, an ionic bond, or a coordination bond. For example, the bond between metal ions and the linkers may be an ionic bond between positively charged (or negatively charged) metal ions and linkers that are negatively charged (or positively charged), on the functional group 126 at one end of the linkers. The bond between the surface layer of the substrate 110 and the linkers may be a spontaneous chemical bond between the functional group 122 of the linkers and the surface of the substrate.

To be more specific, the linkers 120A may be organic molecules that form a self-assembled monomolecular layer (a layer of one molecule or one linker in thickness). In other words, the linkers 120A may be organic molecules having both the functional group 122 that is bonded to the surface layer 114 and the functional group 126 suitable for bonding with metal ions. The linkers 120A may include a chain group 124, which connects the functional group 122 with the functional group 126, and enables the formation of a monomolecular layer aligned by Van Der Waals interactions.

Self-assembly may be achieved by suitably designing the material of the surface of the substrate and the first functional group 122 of the linkers. A set of end groups for materials that are generally known to be self-assembling may be used.

In a specific non-limiting embodiment, when the surface layer 114 of the substrate 110 is made of oxide, nitride, oxynitride, or silicate, the linkers may be a compound represented by the following Formula 1.

$$R1\text{-}C\text{—}R2 \qquad \text{(Formula 1)}$$

In Formula 1, R1 represents a functional group that bonds with the substrate, C represents a chain group, and R2 represents a functional group that bonds with metal ions. R1 may be one or more functional groups selected from acetyl, acetic acid, phosphine, phosphonic acid, alcohol, vinyl, amide, phenyl, amine, acryl, silane, cyan and thiol groups. C is a linear or branched carbon chain having 1 to 20 carbon atoms. R2 may be one or more functional groups selected from carboxylic acid, carboxyl, amine, phosphine, phosphonic acid and thiol groups.

In a non-limiting embodiment, the linkers 120A may be one or more selected from among octyltrichlorosilane (OTS), hexamethyldisilazane (HMDS), octadecyltrichlorosilane (ODTS), (3-aminopropyl)trimethoxysilane (APS), (3-aminopropyl)triethoxysilane, N-(3-aminopropyl)-dimethyl-ethoxysilane (APDMES), perfluorodecyltrichlorosilane (PFS), mercaptopropyltrimethoxysilane (MPTMS), N-(2-aminoethyl)-3aminopropyltrimethoxysilane, (3-trimethoxysilylpropyl) diethylenetriamine, octadecyltrimethoxysilane (OTMS), (heptadecafluoro-1,1,2,2-tetrahydrodecyl)trichlorosilane (FDTS), dichlorodimethylsilane (DDMS), N-(trimethoxysilylpropyl)ethylenediamine triacetic acid, hexadecanethiol (HDT), and epoxyhexyltriethoxysilane.

To ensure stable isolation between the nanoparticles and the substrate, the linkers may include an alkane chain group, particularly an alkane chain group having 3 to 20 carbon atoms, and may further include an oxygen-containing moiety. Examples of the oxygen-containing moiety include ethylene glycol (—O—$CH_2$—$CH_2$—), carboxylic acid (—COOH), alcohol (—OH), ether (—O—), ester (—COO—), ketone (—CO—), aldehyde (—COH) and/or amide (—NH—CO—), etc.

Attachment of the linkers 120A may be performed by bringing the substrate 110 into contact with a solution of linkers 120A in a solvent. The solvent that is used to form the linker solution may be any solvent that may dissolve the linkers and be easily removed by volatilization. As is known in the art, when the linker contains a silane group, water for promoting hydrolysis may be added to the linker solution. It is to be understood that the contact between the substrate and the linker solution may be performed using any method that can form a self-assembled monomolecular layer on a substrate. In a non-limiting embodiment, the contact between the linker solution and the substrate may be performed using a dipping, micro contact printing, spin-coating, roll coating, screen coating, spray coating, spin casting, flow coating, screen printing, ink jet coating or drop casting method.

When metal ions are fixed to the substrate by the linkers 120A, there are advantages in that damage to the surface layer 114 of the substrate may be prevented, and a uniformly distributed metal ion layer may be formed by self-assembly. Also, nanoparticles prepared by application of energy may be stably fixed.

The linkers may have functional groups that are chemically bonded to the metal ions. The surface of the substrate 110 may be modified to form a functional group (linker), and then a metal precursor may be supplied to the surface-modified substrate so that metal ions may bond with the a functional group. The functional group may be one or more selected from carboxylic acid, carboxyl, amine, phosphine, phosphonic acid and thiol groups. Formation of the functional group on the substrate surface may be performed using any method. Specific examples of the method for forming the functional group on the substrate surface include plasma modification, chemical modification, and vapor deposition (application) of a compound having a functional group. Modification of the substrate surface may be performed by vapor deposition (application of a compound having a functional group) to prevent surface layer impurity introduction, quality deterioration, and damage.

In a specific and non-limiting embodiment, when the surface layer 114 of the substrate 110 is formed of an oxide, a nitride, an oxynitride or a silicate, a functional group (linker) may be formed by a silane compound layer on the substrate 110.

The silane compound layer may be made of an alkoxy silane compound having one or more functional groups selected from among carboxylic acid, carboxyl, amine, phosphine, phosphonic acid and thiol groups. The silane compound, which is an example of a linker, may be represented by the following Formula 2:

(Formula 2)

In Formula 2, $R^1$ is hydrogen, a carboxylic acid group, a carboxyl group, an amine group, a phosphine group, a phosphonic acid group, a thiol group, or a linear or branched alkyl group having 1 to 10 carbon atoms; $R^2$ is a linear or branched alkyl group having 1 to 10 carbon atoms; R is a linear or branched alkyl group having 1 to 10 carbon atoms; the alkyl group R may be substituted with one or more selected from among carboxylic acid, carboxyl, amine, phosphine, phosphonic acid and thiol groups; the alkyl group in $R^1$ and the alkyl group in $R^2$ may each be independently substituted with one or more selected from among halogen, carboxylic acid, carboxyl, amine, phosphine, phosphonic acid and thiol groups; and n is 0, 1 or 2.

The silane compound may be represented by one of the following Formulas 3 to 5:

(Formula 3)

(Formula 4)

(Formula 5)

In the Formula 3, 4, and 5, $R^3$ groups are each independently an alkoxy or alkyl group, and one or more $R^3$ groups are an alkoxy group; and $R^4$ is a divalent hydrocarbon group having 1 to 20 carbon atoms. $R^3$ groups in Formula 3, 4 or 5 may be the same or different and may each be independently an alkoxy group, such as methoxy, ethoxy or propoxy, or an alkyl group; and $R^4$ may be a divalent hydrocarbon group having 1 to 20 carbon atoms, such as —$CH_2$—, —$CH_2$—$CH_2$—, —$CH_2$—$CH_2$—$CH_2$—, —$CH_2$—CH($CH_3$)—$CH_2$— or —$CH_2$—$CH_2$—CH($CH_3$)—.

Non-limiting examples of the carboxysilane compound include methyldiacetoxysilane, 1,3-dimethyl-1,3-diacetoxydisiloxane, 1,2-dimethyl-1,2-diacetoxydisilane, 1,3-dimethyl-1,3-dipropionoxydisilamethane, and 1,3-diethyl-1,3-diacetoxydisilamethane. Non-limiting examples of the aminosilane compound include N-(2-aminoethyl)aminopropyltri(methoxy)silane, N-(2-aminoethyl)aminopropyltri(ethoxy)silane, N-(2-aminoethyl)aminopropylmethyldi(methoxy)silane, N-(2-aminoethyl)aminopropylmethyldi(ethoxy)silane, 3-aminopropyl tri(methoxy)silane, 3-aminopropyltri(ethoxy)silane, 3-aminopropylmethyldi(methoxy)silane, and 3-aminopropylmethyldi(ethoxy)silane. Non-limiting examples of the mercaptosilane compound include mercaptopropyltrimethoxysilane, mercaptopropyltriethoxysilane, mercaptoethyltrimethoxysilane, and mercaptoethyltriethoxysilane.

The above-described silane compound may be applied to or deposited on the surface of the substrate 110 to form a silane compound layer (i.e. a linker layer). The silane compound layer may be formed by applying and drying a silane compound solution. Alternatively, the silane compound may be deposited by supplying a gaseous silane compound to the substrate surface.

As the silane compound functional groups will react with a metal precursor to be supplied later to fix metal ions to the substrate, it is preferred to form a silane compound layer where the functional groups are uniformly exposed to the surface. The silane compound layer may be formed by atomic layer deposition (ALD).

The above-described silane compounds having a functional group (particularly the silane compound of Formulas 2, 3, and 4) may belong to the above-described self-assembly molecule group. Specifically, $(R^3)_3Si$ may correspond to the functional group that is bonded to the substrate surface, $R^4$ may correspond to the chain group, and R (R in formula 2) such as —SH, —COOH or —$NH_2$ may correspond to the functional group that bonds with metal ions. The silane compound layer (i.e. the linker layer) may be a monomolecular layer.

Figure 2B:
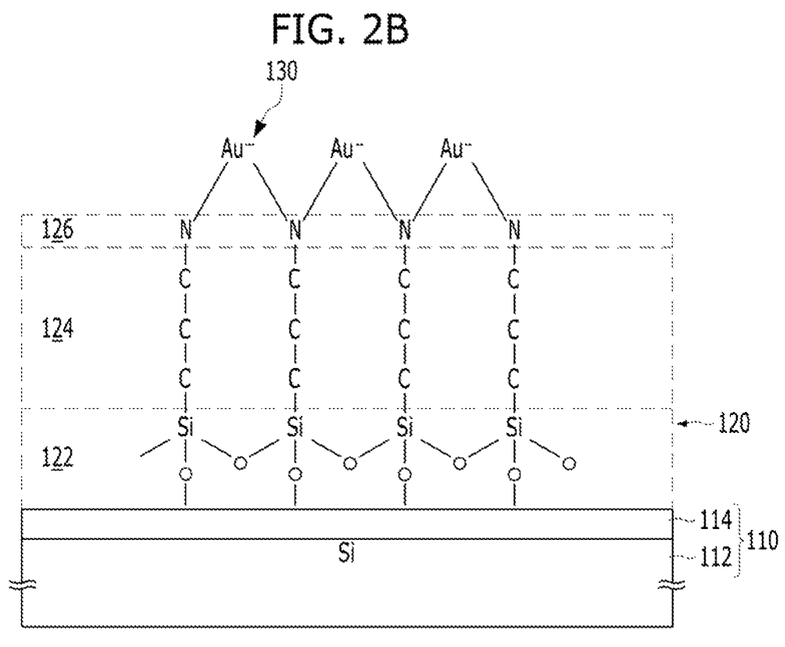
Figure 2C:
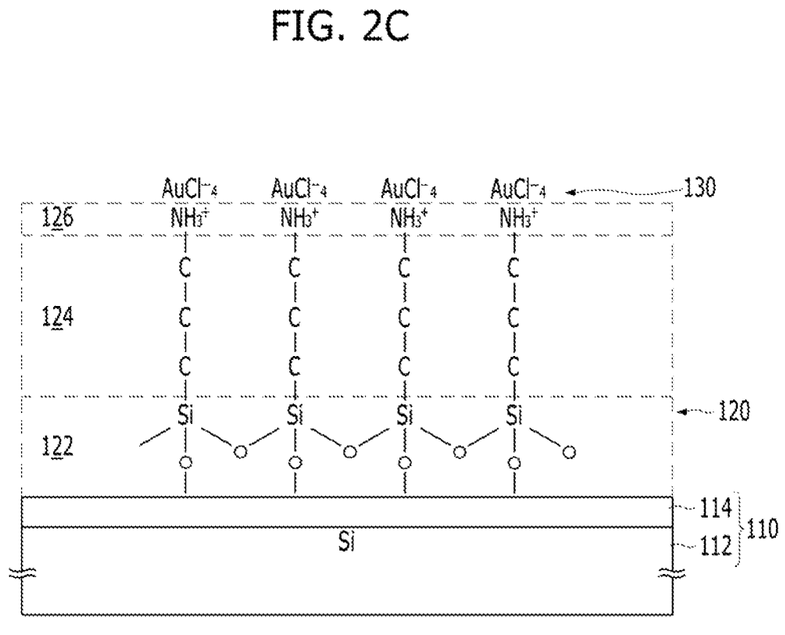

FIGS. 2B and C show metal ions 130 bonded to the linkers 120A. The metal ions 130 may be bonded to the functional group 126 of the linkers 120A.

The metal ions 130 may be formed by supplying a metal precursor to the linkers. In other words, the metal ions 130 may be formed by applying a metal precursor solution to the substrate or applying a gaseous metal precursor to the substrate.

The metal precursor may be designed to suit the type of nanoparticles that are desired. For example, the metal precursor may be one or more metals selected from among transition metals, post-transition metals, and metalloids. In a non-limiting embodiment, the transition metal precursor may be a transition metal salt. Specifically, the transition metal may be one or more selected from among Au, Ag, Ru, Pd and Pt, and the transition metal salt may be selected from among halides, chalcogenides, hydrochlorides, nitrates, sulfates, acetates or ammonium salts of the transition metal. When the transition metal of the transition metal precursor is Au, examples of the transition metal precursor include, but are not limited to, $HAuCl_4$, $AUCl$, $AUCl_3$, $AU_4Cl_8$, $KAuCl_4$, $NaAuCl_4$, $NaAuBr_4$, $AuBr_3$, $AuBr$, $AuF_3$, $AuF_6$, $AUI$, $AuI_3$, $KAu(CN)_2$, $Au_2O_3$, $Au_2S$, $Au_2S_3$, $AuSe$, $Au_2Se_3$, and the like. However, the scope of the present disclosure is not limited to these examples.

The metal ions 130 that are bonded (attached) to the substrate by the linkers 120A may be ions of one or more metals selected from among transition metals, post-transition metals, and metalloids. Depending on the kind of metal precursor, the metal ions 130 may be the above-described metal ions themselves or ions including the above-described metals. Metal ions 130 themselves may be bonded to the functional groups 126 of the linkers (see FIG. 2B), or metal-containing ions may be bonded to the functional groups 126 of organic molecules (see FIG. 2C). The metal-containing ions may originate from the metal precursor in its reaction with the functional groups of the organic molecules.

Figure 2D:
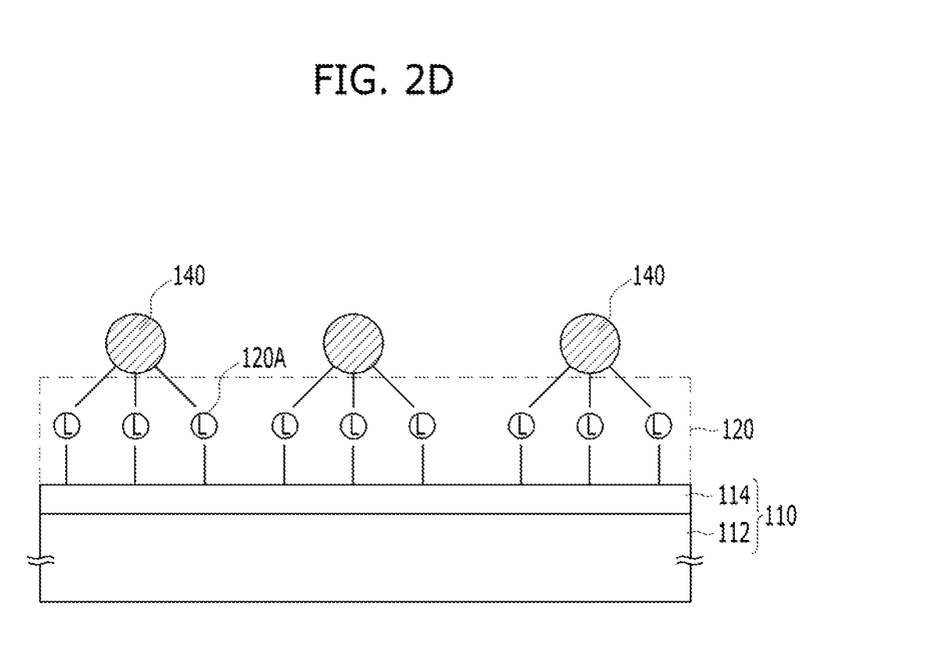

FIG. 2D shows metallic nanoparticles 140 formed by the reduction and growth of the metal ions 130 by application of energy. The metallic nanoparticles 140 may be attached to the substrate 110 by the linkers 120A.

Advanced technology enables the synthesis of very fine nanoparticles of tens to hundreds of atoms, but due to thermodynamics, synthesized nanoparticles may not have a uniform particle size distribution and the difference in size between the nanoparticles may increase as the size of the reaction field during synthesis increases. In addition, a method of preparing nanoparticles by etching using a top-down process enables the preparation of particles having a size of about 20 nm or less by advanced lithography, but it is difficult to apply commercially because the process is complicated and precise control is required.

However, in the fabrication method according to the first embodiment, nanoparticles are prepared directly in a very small reaction field corresponding to the surface region of the substrate, and thus nanoparticles having a very uniform and finely controlled size may be prepared at high density. Because nanoparticles are prepared by fixing metal atoms (ions) to the substrate by the linkers and then applying energy to the metal ions, the nanoparticles may be quickly produced in a simple, easy and cost-effective manner. Further, because nucleation and growth (formation of nanoparticles) are induced by application of energy in a state where metal atoms (ions) are fixed to the substrate by the linkers, the migration of the metal atoms (ions) may be controlled resulting in the formation of more uniform and fine nanoparticles.

The metal material used for nucleation and growth to form nanoparticles may be supplied solely by the metal atoms (ions) bonded to the linkers. In other words, the supply of material used to form nanoparticles comes from the diffusion of the metal atoms (ions) bonded to the linkers. Due to bonding of the metal atoms (ions) to the linkers, the metal atoms (ions) are slowed in migrating beyond a predetermined distance to participate in nucleation and growth, and thus the reaction field of each nanoparticle may be limited to around the nucleus. Therefore, nanoparticles may be formed smaller, with more uniform size, more uniform separation distance, and at a higher density. In addition, bonding of the metallic nanoparticles to the linkers is maintained, allowing the nanoparticles to be stably fixed to the substrate by the linkers. The separation distance between the nanoparticles may correspond to the diffusion distance of the metal atoms that participate in the nucleation and growth of the nanoparticles.

Energy that is applied to form the nanoparticles may be one or more selected from among heat energy, chemical energy, light energy, vibration energy, ion beam energy, electron beam energy, and radiation energy.

Thermal energy may include Joule heat and may be applied directly or indirectly. Direct application of thermal energy may be performed in a state in which a heat source and the substrate having metal ions fixed thereto come into physical contact with each other. Indirect application of thermal energy may be performed in a state in which a heat source and the substrate having metal ions fixed thereto do not come into physical contact with each other. Non-limiting examples of direct application include a method of placing a heating element, which generates Joule heat by the flow of electric current, beneath the substrate and transferring thermal energy to the metal ions through the substrate. Non-limiting examples of indirect application include a method that uses a conventional heat-treatment furnace including a space in which an object (such as a tube) to be heat-treated is placed, a heat insulation material that surrounds the space to prevent heat loss, and a heating element placed inside the heat insulation material. A non-limiting example of indirect heat application is seen in the method of placing a heating element at a predetermined distance above the substrate, where the metal ions are fixed, and transferring thermal energy to the metal ions through a fluid (including air) present between the substrate and the heating element.

Light energy may include light having a wavelength ranging from extreme ultraviolet to near-infrared, and application of light energy may include irradiation with light. In a non-limiting embodiment, a light source may be placed above the substrate, having the metal ions fixed thereto, at a predetermined distance from the metal ions, and light from the light source may be irradiated onto the metal ions.

Vibration energy may include microwaves and/or ultrasonic waves. Application of vibration energy may include irradiation with microwaves and/or ultrasonic waves. In a non-limiting embodiment, a microwave and/or ultrasonic wave source may be placed above the substrate, having the metal ions fixed thereto, at a predetermined distance from the metal ions, and microwaves and/or ultrasonic waves from the source may be irradiated onto the metal ions.

Radiation energy may include one or more selected from among α rays, β rays and γ rays. In a non-limiting embodiment, a radiation source may be placed above the substrate, having the metal ions fixed thereto, at a predetermined distance from the metal ions, and radiation from the source may be irradiated onto the metal ions.

Energy may be kinetic energy of a particle beam, and the particle beam may include an ion beam and/or an electron beam. The ions of the beam may be negatively charged. In a non-limiting embodiment, an ion or electron source may be placed above the substrate, having the metal ions fixed thereto, at a predetermined distance from the metal ions, and an ion beam and/or electron beam may be applied to the metal ions using an accelerating element that provides an electric field (magnetic field) that accelerates ions or electrons in the direction of the metal ions.

Chemical energy is the Gibbs free energy difference between before and after a chemical reaction, and the chemical energy may include reduction energy. Chemical energy may include the energy of a reduction reaction with a reducing agent and may mean the energy of a reduction reaction in which the metal ions are reduced by the reducing agent. In a non-limiting embodiment, application of chemical energy may be a reduction reaction in which the reducing agent is brought into contact with the substrate having the metal ions fixed thereto. The reducing agent may be supplied in the liquid or gaseous state.

In a fabrication method according to an embodiment, application of energy may include simultaneously or sequentially applying two or more selected from among heat energy, chemical energy, light energy, vibration energy, ion beam energy, electron beam energy, and radiation energy.

In a specific embodiment of simultaneous application, application of heat may be performed simultaneously with application of a particle beam. It is to be understood that the particles of the particle beam may be heated by heat energy. In another specific embodiment of simultaneous application, application of heat may be performed simultaneously with application of a reducing agent. In still another embodiment of simultaneous application, application of a particle beam may be performed simultaneously with application of infrared rays or with application of microwaves.

Sequential application may mean that one kind of energy is applied followed by application of another kind of energy. It may also mean that different kinds of energy are continuously or discontinuously applied to the metal ions. It is preferable that reduction of the metal ions fixed to the substrate by the linkers be performed before formation of nanoparticles, and thus in a specific embodiment of sequential application, heat may be applied after addition of a reducing agent or after application of a positively charged particle beam.

In a non-limiting practical embodiment, application of energy may be performed using a rapid thermal processing (RTP) system, including a tungsten-halogen lamp, and the rapid thermal processing may be performed at a heating rate of 50 to 150° C./sec. Also, rapid thermal processing may be performed in a reducing atmosphere or an inert gas atmosphere.

In a non-limiting practical embodiment, application of energy may be performed by bringing a solution of a reducing agent in a solvent into contact with the metal ions followed by thermal processing using a rapid thermal processing system in a reducing atmosphere or an inert gas atmosphere.

In a non-limiting practical embodiment, application of energy may be performed by generating an electron beam from an electron beam generator in a vacuum chamber and accelerating the generated electron beam to the metal ions. The electron beam generator may be of a square type or a linear gun type. The electron beam may be produced by generating plasma from the electron beam generator and extracting electrons from the plasma using a shielding membrane. In addition, it is to be understood that a heating element may be provided on a holder for supporting the substrate in the vacuum chamber, and heat energy may be applied to the substrate by this heating element before, during and/or after application of the electron beam.

When the desired nanoparticles are metal nanoparticles, the metal nanoparticles may be prepared in situ by application of energy as described above. When the nanoparticles to be prepared are not metal nanoparticles, but are metal compound nanoparticles, the metal compound nanoparticles may be prepared by supplying a substance different from the metal ions during or after application of the above-described energy. Specifically, the metal compound nanoparticles may include metal oxide nanoparticles, metal nitride nanoparticles, metal carbide nanoparticles or intermetallic compound nanoparticles. More specifically, the metal compound nanoparticles may be prepared by supplying a different substance in the gaseous or liquid state during or after application of the above-described energy. In a specific embodiment, metal oxide nanoparticles in place of metal nanoparticles may be prepared by supplying an oxygen source including oxygen gas during application of energy.

In addition, metal nitride nanoparticles in place of metal nanoparticles may be prepared by supplying a nitrogen source including nitrogen gas during application of energy. Metal carbide nanoparticles may be prepared by supplying a carbon source, including $C_1$-$C_{10}$ hydrocarbon gas during application of energy, and intermetallic compound nanoparticles may be prepared by supplying a precursor gas containing a different substance, which provides an intermetallic compound, during application of energy. Specifically, the intermetallic compound nanoparticles may be prepared by carbonizing, oxidizing, nitrifying or alloying the metal nanoparticles prepared by application of the above-described energy.

The density of nanoparticles (the number of nanoparticles per unit surface area of the channel region) and the particle size and particle size distribution may be controlled by one or more factors including the kind, magnitude, temperature, and duration of energy applied.

To be specific, nanoparticles having an average particle diameter of about 0.5 nm to 3 nm may be fabricated by applying energy. In this case, uniform nanoparticles may be prepared with a particle radius standard deviation of about ±20% or less. Also, highly dense nanoparticles having a nanoparticle density (which is the number of the nanoparticles per unit area) of about $10^{13}$ to $10^{15}$/cm² may be prepared.

According to an embodiment, when the applied energy is an electron beam, the electron beam may be irradiated at a dose of about 0.1 KGy to 100 KGy. With this irradiation dose of an electron beam, nanoparticles having an average particle diameter of about 2 to 3 nm may be prepared, and the nanoparticles may have a particle radius standard deviation of about ±20% or less. The nanoparticle density (which is the number of the nanoparticles per unit area) may range from about $10^{13}$ to $10^{15}$/cm².

According to another embodiment, when the applied energy is an electron beam, the electron beam may be irradiated at a dose of about 100 μGy to 50 KGy. With this irradiation dose of an electron beam, nanoparticles having an average particle diameter of about 1.3 to 1.9 nm may be prepared, and the nanoparticles may have a particle radius standard deviation of about ±20% or less. The nanoparticle density (which is the number of the nanoparticles per unit area) may range from about $10^{13}$ to $10^{15}$/cm², and specifically, from about $0.2 \times 10^{14}$ to $2 \times 10^{15}$/cm².

According to another embodiment, when the applied energy is an electron beam, the electron beam may be irradiated at a dose of about 1 μGy to 10 KGy. With this irradiation dose of an electron beam, nanoparticles having an average particle diameter of about 0.5 to 1.2 nm may be prepared, and the nanoparticles may have a particle radius standard deviation of about ±20% or less. The nanoparticle density (which is the number of the nanoparticles per unit area) may range from about $10^{13}$ to $10^{15}$/cm², and specifically, from about $0.2 \times 10^{14}$ to $0.3 \times 10^{15}$/cm².

According to another embodiment, when the applied energy is heat energy, nanoparticles having an average particle diameter of about 2 to 3 nm may be prepared by performing a heat treatment in a reducing atmosphere at a temperature of about 100 to 500° C. for about 0.5 to 2 hours or by supplying a reducing agent to the metal ions bonded to the linkers and performing a heat treatment in an inert gas atmosphere at a temperature of about 200 to 400° C. for about 0.5 to 2 hours. The prepared nanoparticles may have a particle radius standard deviation of about ±20% or less. The nanoparticle density (which is the number of the nanoparticles per unit area) may range from about $10^{13}$ to $10^{15}$/cm².

According to another embodiment, when the applied energy is heat energy, nanoparticles having an average particle diameter of about 1.3 to 1.9 nm may be prepared by performing a heat treatment in a reducing atmosphere at a temperature of about 200 to 400° C. for about 0.5 to 2 hours or by supplying a reducing agent to the metal ions bonded to the linkers and performing a heat treatment in an inert gas atmosphere at a temperature of about 100 to 300° C. for about 0.5 to 2 hours. The nanoparticles may have a particle radius standard deviation of about ±20% or less. The nanoparticle density (which is the number of the nanoparticles per unit area) may range from about $10^{13}$ to $10^{15}/cm^2$, and specifically, the nanoparticle density may range from about $0.2 \times 10^{14}$ to $0.2 \times 10^{15}/cm^2$.

According to another embodiment, when the applied energy is heat energy, nanoparticles having an average particle diameter of about 0.5 to 1.2 nm may be prepared by performing a heat treatment in a reducing atmosphere at a temperature of about 200 to 400° C. for about 0.2 to 1 hour or by supplying a reducing agent to the metal ions bonded to the linkers and performing a heat treatment in an inert gas atmosphere at a temperature of about 100 to 300° C. for about 0.2 to 1 hour. The prepared nanoparticles may have a particle radius standard deviation of about ±20% or less. The nanoparticle density (which is the number of the nanoparticles per unit area) may range from about $10^{13}$ to $10^{15}/cm^2$, and specifically, from about $0.2 \times 10^{14}$ to $0.3 \times 10^{15}/cm^2$.

According to another embodiment, when the applied energy is chemical energy, nanoparticles having an average particle diameter of about 2 to 3 nm may be prepared by performing a chemical reaction induced by a reducing agent at a reaction temperature of about 20 to 40° C. for about 0.5 to 2 hours. The prepared nanoparticles may have a particle radius standard deviation of about ±20% or less. The nanoparticle density (which is the number of the nanoparticles per unit area) may range from about $10^{13}$ to $10^{15}/cm^2$.

According to another embodiment, when the applied energy is chemical energy, nanoparticles having an average particle diameter of about 1.3 to 1.9 nm may be prepared by performing a chemical reaction induced by a reducing agent at a reaction temperature of about −25 to 5° C. for about 0.5 to 2 hours. The prepared nanoparticles may have a particle radius standard deviation of about ±20% or less. The nanoparticle density (which is the number of the nanoparticles per unit area) may range from about $10^{13}$ to $10^{15}/cm^2$, and specifically, from about $0.2 \times 10^{14}$ to $0.2 \times 10^{15}/cm^2$.

According to another embodiment, when the applied energy is chemical energy, nanoparticles having an average particle diameter of about 0.5 to 1.2 nm may be prepared by performing a chemical reaction induced by a reducing agent at a reaction temperature of about −25 to 5° C. for about 0.2 to 1 hour. The prepared nanoparticles may have a particle radius standard deviation of about ±20% or less. The nanoparticle density (which is the number of the nanoparticles per unit area) may range from about $10^{13}$ to $10^{15}/cm^2$, and specifically, from about $0.2 \times 10^{14}$ to $0.3 \times 10^{15}/cm^2$.

As described above, nanoparticles may be grown by applying heat energy and/or chemical energy in a reducing atmosphere. When heat energy is applied in a reducing atmosphere, the reducing atmosphere may contain hydrogen. In a specific embodiment, the reducing atmosphere may be an inert gas containing about 1 to 5% of hydrogen. Heat energy may be applied in an atmosphere in which a reducing gas flows to provide uniform reduction. In a specific embodiment, the atmosphere may have reducing gas flowing at a flow rate of about 10 to 100 cc/min.

When chemical energy and heat energy are sequentially applied, a reducing agent may be brought into contact with the metal ions, followed by application of heat energy in an inert atmosphere. The reducing agent may be any compound that reduces the metal ions into a metal. When chemical energy is applied by addition of the reducing agent, transition metal nanoparticles may also be formed by a reduction reaction. When nanoparticles are to be formed from the metal ions by a reduction reaction, the reduction reaction should occur very rapidly and uniformly throughout the channel region so that transition metal particles are more uniform in size.

A strong reducing agent may be used, and in a preferred embodiment, the reducing agent may be $NaBH_4$, $KBM_4$, $N_2H_4H_2O$, $N_2H_4$, $LiAlH_4$, HCHO, $CH_3CHO$, or a mixture of two or more thereof. Also, when chemical energy is applied, the size of the nanoparticles may be controlled by adjusting the chemical reaction temperature and controlling the nucleation rate and the growth of the nanoparticles when a strong reducing, as described above, is used. The contact between the metal ions bonded to the linkers and the reducing agent may be achieved either by applying a solution of the reducing agent dissolved in a solvent to the metal ion bonded region, or by impregnating the substrate with a solution of the reducing agent dissolved in a solvent, or by supplying the reducing agent in the gaseous phase to the substrate. In a specific non-limiting embodiment, the contact between the reducing agent and the metal ions may be performed at room temperature for about 1 to 12 hours.

As described above, the nucleation and growth of transition metal nanoparticles may be controlled by one or more factors selected from among the kind, magnitude, and time of the applied energy.

It is possible to prepare not only metallic nanoparticles but also metal oxide nanoparticles, metal nitride nanoparticles, metal carbide nanoparticles, or intermetallic compound nanoparticles by supplying a substance other than metal ions while energy is applied or after energy is applied to change the metallic nanoparticles into metallic compound nanoparticles. For clarity, the metal ions are grown (i.e. reduced, formed, changed, etc.) into metallic nanoparticles by the application of energy. This does not happen to all metal ions instantaneously and therefore an organic surfactant, or other material, may be added during this growth period (i.e. during the application of energy or during a pause in energy application) to a mixture of metallic nanoparticles (which have been grown by the application of energy) and metal ions (which have yet to be grown/reduced/etc).

This addition of material (e.g. a dielectric organic material, a surfactant, oxygen, carbon source, etc.) may result in a nanostructure having desirable characteristics. In non-limiting examples: (1) a chemical reaction may take place between the metallic nanoparticles and the material that is introduced, resulting in nanoparticles of a different composition, perhaps oxidized nanoparticles; (2) the material that is introduced may simply bond to the substrate, metal ions, or nanoparticles to control the migration of metallic nanoparticles or metal ions, resulting in finer sized and more uniform nanoparticles. This result is possible because during the application of energy metal ions can diffuse on the nanostructure and agglomerate to form nanoparticles. The addition of material may physically inhibit (partially) the diffusion of metal ions and shrink the reaction field, allowing less metal ions to agglomerate, resulting in finer and more uniform nanoparticles.

In a fabrication method according to an embodiment, the size of nanoparticles may be controlled by supplying an organic surfactant that is to be bonded to or adsorbed on the metal ions, followed by application of energy. Otherwise, the size of nanoparticles may be controlled during the growth thereof by supplying an organic surfactant that is to be bonded to or adsorbed on the metal ions during application of energy. This supply of the organic surfactant may be optionally performed during the fabrication process. As the organic surfactant that is applied before or during application of energy, one or more organic surfactants may be used.

To more effectively inhibit the mass transfer of the metal ions, a first organic material and a second organic material that are different from each other may be used as the surfactant.

The first organic material may be a nitrogen- or sulfur-containing organic compound. For example, the sulfur-containing organic material may include a linear or branched hydrocarbon compound having a thiol group at one end. In a specific example, the sulfur-containing organic compound may be one or more selected from among HS—$C_n$—$CH_3$ (n: an integer ranging from 2 to 20), n-dodecyl mercaptan, methyl mercaptan, ethyl mercaptan, butyl mercaptan, ethylhexyl mercaptan, isooctyl mercaptan, tert-dodecyl mercaptan, thioglycolacetic acid, mercaptopropionic acid, mercaptoethanol, mercaptopropanol, mercaptobutanol, mercaptohexanol and octyl thioglycolate.

The second organic material may be a phase-transfer catalyst-based organic compound, for example, quaternary ammonium or a phosphonium salt. More specifically, the second organic surfactant may be one or more selected from among tetraocylyammonium bromide, tetraethylammonium, tetra-n-butylammonium bromide, tetramethylammonium chloride, and tetrabutylammonium fluoride.

The organic surfactant that is applied before or during application of energy may be bonded to or adsorbed on the nuclei of metal ions or the metal ions bonded to the linkers, and the nucleation and growth of nanoparticles by energy applied may be controlled by the organic surfactant that is bonded to or adsorbed on the metal ions. This organic surfactant makes it possible to inhibit the mass transfer of the metal ions during application of energy to thereby form more uniform and finer nanoparticles. Because the metal ions bond with the organic surfactant, these metal ions require higher activation energy compared to when they would otherwise diffuse to participate in nucleation or growth, or the diffusion thereof is physically inhibited by the organic surfactant. Thus, the diffusion of the metal atoms (ions) may be slowed and the number of the metal atoms (ions) that participate in the growth of nuclei may be decreased.

The process of applying energy in the presence of the organic surfactant may include, before application of energy, applying a solution of the organic surfactant to the channel region (i.e., the substrate surface having the metal ions bonded thereto by the linkers) or supplying the organic surfactant in the gaseous state to the channel region. Alternatively, it may include, together with application of energy, applying a solution of the organic surfactant to the channel region having the metal ions formed therein or supplying the organic material in the gaseous state to the channel region to bond or adsorb the organic surfactant to the metal nuclei.

Alternatively, it may include, during application of energy, applying a solution of the organic surfactant to the channel region having the metal ions formed therein or supplying the organic material in the gaseous state to the channel region to bond or adsorb the organic surfactant to the metal nuclei. Alternatively, it may include, after application of energy for a predetermined period of time and while pausing energy application, applying a solution of the organic surfactant to the channel region having the metal ions formed therein or supplying the organic material in the gaseous state to the channel region to bond or adsorb the organic surfactant to the metal nuclei, followed by re-application of energy.

In a fabrication method according to the first embodiment, energy may be applied to the entire area or a portion of the region having the metal ions bonded thereto. When energy is applied to a portion of the region, energy may be irradiated in a spot, line or predetermined plane shape. In a non-limiting embodiment, energy may be applied (irradiated) in spots while the metal ion-bonded region may be entirely scanned. Application of energy to a portion of the metal ion-bonded region may include not only a case in which energy is irradiated in a spot, line or plane shape while the metal ion-bonded region is entirely scanned, but also in a case in which energy is applied (irradiated) only to a portion of the metal ion-bonded region. As described above, a pattern of nanoparticles may be formed by applying energy to a portion of the channel region. In other words, application (irradiation) of energy to a portion of the channel region makes it possible to form a pattern of nanoparticles.

Figure 2E:
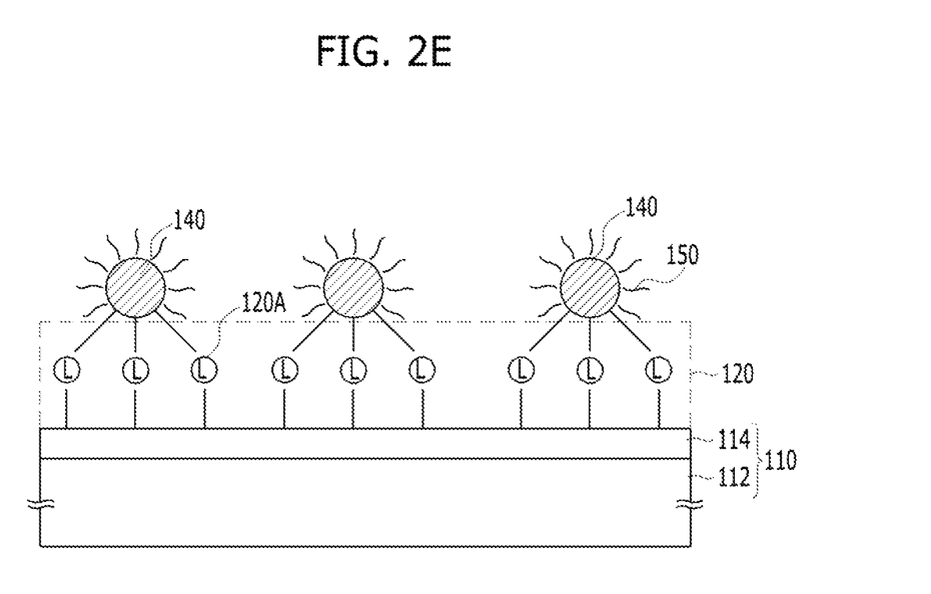

FIG. 2E shows the receptors 150 bonded to the metallic nanoparticles 140. The receptors 150 may be bonded to or coat the surfaces of the metallic nanoparticles 140. All materials suitable for being both bonded to the surface of the metallic nanoparticles 140 and reacting with a marker (e.g. e-m waves, a molecule, etc.) to be sensed through a physical, optical, electrical, and/or chemical mechanism may be used as the receptors 150.

The marker may be a protein, a nucleic acid, an oligosaccharide, an amino acid, carbohydrates, a solution gas, a sulfur oxide gas, a nitrogen oxide gas, pesticide residue, a heavy metal, and an environmentally harmful substance. The receptors 150 suitable for responding to a marker may be an enzyme substrate, a ligand, an amino acid, a peptide, a protein, a nucleic acid, a lipid, or carbohydrates. The receptors 150 may be bonded to or coat the surfaces of the grown metallic nanoparticles 140 through functional groups. The functional groups of the receptors 150 may be at least one selected from an amine group, a carboxylic acid group, and a thiol group.

Referring to FIG. 2E, the sensor fabricated through the fabrication method in accordance with the first embodiment will be described in detail.

The sensor in accordance with the first embodiment includes a nanostructure for physical, electrical, chemical, and optical sensing of a marker (which may be a target material, EM waves, etc).

The nanostructure may include a substrate 110, linkers 120A formed over the substrate 110, and metallic nanoparticles 140 that are grown from metal ions bonded to the linkers 120A. The nanostructure may further include receptors 150 bonded to the surface of the metallic nanoparticles 140. On the surface of the metallic nanoparticles 140, an organic surfactant may be bonded before or while the nanoparticles are being grown, and may remain afterwards.

The substrate 110 may include a surface layer 114, which may be metal thin film or a transition metal including a noble metal, a metal, or a mixture thereof. According to another embodiment, the substrate 110 may be a flexible substrate, which may include a surface layer having hydroxyl (—OH) functional groups.

The linkers 120A may be organic molecules bonded to the surface of the substrate 110 through self-assembly. The nanostructure may include a linker layer 120 formed of the linkers 120A bonded to the surface of the substrate 110. The linker layer 120 may be a self-assembled monomolecular layer formed on the surface of the substrate 110. Also, the linker layer 120 may be a silane compound layer and the linkers 120A may include one functional group selected from an amine group, a carboxylic acid group, and a thiol group. The linkers 120A may be selected according to the surface layer 114 of the substrate.

The metallic nanoparticles 140 may be selected from metal nanoparticles, metal oxide nanoparticles, metal nitride nanoparticles, metal carbide nanoparticles, and intermetallic compound nanoparticles. The metallic nanoparticles 140 may be formed by bonding metal ions to the linkers 120A and then growing the metal ions.

The size of the metallic nanoparticles 140 may be controlled according to the energy application conditions while the metallic nanoparticles 140 are grown. Also, the size of nanoparticles may be controlled before the energy for growing the metallic nanoparticles 140 is applied or while applying the energy by whether a surfactant is supplied. The surfactant may be an organic surfactant, and the surfactant may remain on the surface of the metallic nanoparticles 140 after the growing of the metallic nanoparticles 140 is finished. According to an embodiment, when no organic surfactant is used, the metallic nanoparticles 140 may have a particle diameter of about 2.0 to 3.0 nm. According to another embodiment, when a single kind of organic surfactant is used, the metallic nanoparticles 140 may have a particle diameter of about 1.3 to 1.6 nm. According to another embodiment, when multiple kinds of organic surfactant are used, the metallic nanoparticles 140 may have a particle diameter of about 0.5 to 1.2 nm.

The metallic nanoparticles 140 may be arranged separately from each other on the same plane to form a single monomolecular layer. This is possible because the nanoparticle layer is formed by applying energy to an ion layer (a layer of metal ions) that is attached to the linkers. Since the nanoparticle layer is formed by applying energy to the single ion layer formed through a bond with the linkers, agglomeration between the nanoparticles is prevented so that the nanoparticles may form a single layer of nanoparticles that are separated from each other. The nanoparticle layer may be formed of extremely fine nanoparticles at high density.

To be specific, the nanoparticles of the nanoparticle layer may have an average particle size of about 0.5 to 3 nm, and a particle radius standard deviation of equal to or less than about ±20%, which indicates that the size of the nanoparticles is very uniform. Also, the density of the nanoparticles, which is the number of the nanoparticles per unit area, ranges from about $10^{13}$ to $10^{15}/cm^2$, which is very high.

All materials suitable for reacting with a marker may be used as receptors 150. Examples of markers include a protein, a nucleic acid, an oligosaccharide, an amino acid, carbohydrates, a solution gas, a sulfur oxide gas, a nitrogen oxide gas, pesticide residue, a heavy metal, and an environmentally harmful substance. The receptors 150 may be bonded to or coat the surface of the grown metallic nanoparticles 140. The receptors 150 suitable for bonding to the surface of the metallic nanoparticles 140 through functional groups. The receptors 150 may be at least one selected from an enzyme substrate, a ligand, an amino acid, a peptide, a protein, a nucleic acid, a lipid, and carbohydrates. The functional groups of the receptors 150 may be at least one selected from an amine group, a carboxylic acid group, and a thiol group.

The nanostructure may have a vertical multi-stack structure where the linker layer 120 and the nanoparticle layer, where the receptors 150 are bonded, are stacked alternately and repeatedly.

Nanostructure and Fabrication Method Thereof in Accordance with a Second Embodiment of the Present Invention FIGS. 3A to 3D are cross-sectional views illustrating a method for fabricating a sensor platform in accordance with a second embodiment. This embodiment also focuses on the fabrication of a nanostructure that is a sensing element of a sensor.

Figure 3A:
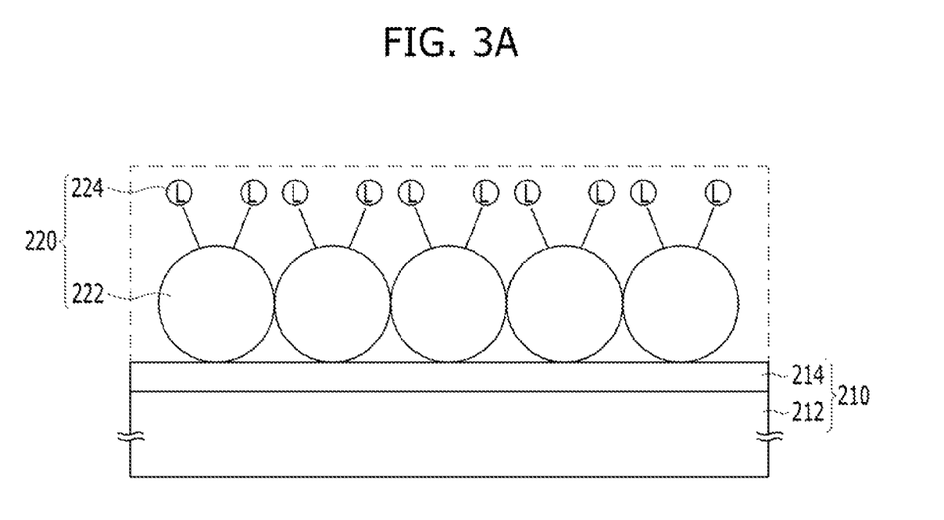
FIGS. 3A to 3D are cross-sectional views illustrating a method for fabricating a sensor platform in accordance with a second embodiment.
Figure 3B:
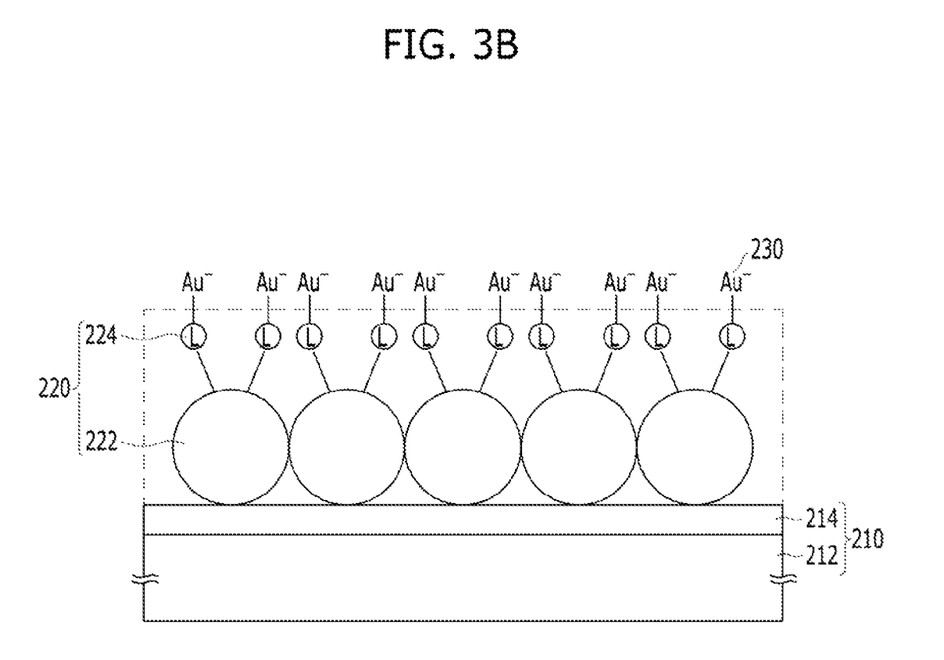
Figure 3C:
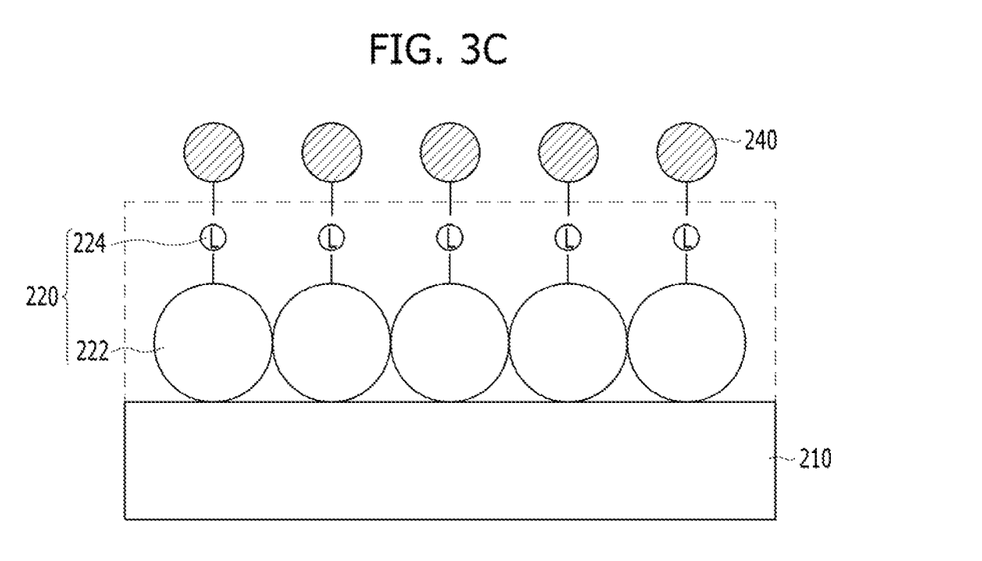

The method for fabricating the sensor platform in accordance with the second embodiment may include forming dielectric material particle supporters 222 on the substrate 210 and then bonding linkers 224 to the dielectric material particle supporters 222 (see FIG. 3A), bonding metal ions 230 to the linkers 224 (see FIG. 3B), and forming metallic nanoparticles 240 out of the metal ions 230 by applying energy (see FIG. 3C). The method may further include bonding receptors 250 to the surface of the metallic nanoparticles 240. Also, the method may further include supplying an organic surfactant of one or more kinds before or during the application of energy.

FIG. 3A shows the dielectric material particle supporters 222 with the linkers 224 bonded thereto formed over the substrate 210. The substrate 210 may include a surface layer 214. The substrate 210 may be a silicon substrate 212 having a silicon oxide ($SiO_2$) dielectric layer as the surface layer 214.

The substrate 210 may be a flexible substrate or a transparent substrate. When the substrate 210 is a flexible substrate, the surface layer 214 of the substrate 210 may be an organic substance having a hydroxyl (—OH) functional groups. The shapes and materials of the substrate 210 may be as diverse as described in the first embodiment.

The dielectric material particle supporters 222 with the linkers 224 bonded thereto may be formed in plural over the substrate 210 to form a supporter layer 220. A method for forming the supporter layer 220 may include preparing a supporter layer material by mixing a dielectric material particle supporters 222 and linkers 224, and depositing or applying the supporter layer material on or to the substrate 210. The supporter layer material may be spin-coated on the substrate 210, or a liquid deposition method of immersing the substrate 210 in a solution where the supporter layer material is dissolved may be used.

The dielectric material particle supporter 222 may include an oxide having at least one element selected from metals, transition metals, post-transition metals, and metalloids. Also, the dielectric material particle supporter 222 may include at least one material selected from a silicon oxide, a hafnium oxide, an aluminum oxide, a zirconium oxide, a barium-titanium composite oxide, an yttrium oxide, a tungsten oxide, a tantalum oxide, a zinc oxide, a titanium oxide, a tin oxide, a barium-zirconium composite oxide, a silicon nitride, a silicon oxynitride, a zirconium silicate, a hafnium silicate and polymers.

The linkers 224 may be organic molecules that are suitable for chemically bonding or adsorbing on the surface of the dielectric material particle supporters 222 and of being chemically bonded to the metal ions 230. To be specific, the linkers 224 may be organic molecules that include a first functional group suitable for being chemically bonded to or adsorbed on the surface of the dielectric material particle supporters 222 and a second functional group suitable for being chemically bonded to metal ions, which are to be formed subsequently. The linkers 224 may also include a chain functional group for connecting the first functional group and the second functional group to each other. The linkers 224 may include one functional group suitable for being bonded to metal ions which may be selected from an amine group, a carboxylic acid group, and a thiol group. The linkers 224 may be formed of the same or similar materials through the diverse methods described in the first embodiment.

FIG. 3B shows metal ions 230 bonded to the linkers 224. The metal ions 230 may be bonded to the functional groups of the linkers 224. The metal ions 230 may be formed by supplying a metal precursor to the substrate (having the linkers formed thereon). To be specific, the metal ions 230 may be formed by applying a metal precursor solution to the substrate 210 or applying a gaseous metal precursor to the substrate 210. The method for bonding the metal ions 230 to the linkers 224 and the materials used for the method may be as diverse as described in reference to the first embodiment.

FIG. 3C shows metallic nanoparticles 240 formed by applying energy and growing (i.e. reducing and agglomerating) the metal ions 230. The energy that is applied to form the nanoparticles may be one or more selected from among heat energy, chemical energy, light energy, vibration energy, ion beam energy, electron beam energy, and radiation energy. The diverse embodiments may be the same as or similar to those of the first embodiment.

In a fabrication method according to the second embodiment, the size of nanoparticles may be controlled by supplying an organic surfactant that is to be bonded to or adsorbed on the metal ions, followed by application of energy. Otherwise, the size of nanoparticles may be controlled during the growth thereof by supplying an organic surfactant that is to be bonded to or adsorbed on the metal ions during application of energy. This supply of the organic surfactant may be optionally performed during the fabrication process. The organic surfactant that is applied before or during the application of energy may be a single organic material or multiple different kinds of organic material.

The organic surfactant that is applied before or during the application of energy may be bonded to or adsorbed on the nuclei of metallic nanoparticles or the metal ions, and the nucleation and growth of nanoparticles by energy applied may be controlled by the organic surfactant that is bonded to or adsorbed on the metal ions. In short, the size of the metallic nanoparticles 240 may be controlled to be uniform and fine.

To more effectively inhibit the transfer of the metal ions, a first organic material and a second organic material of different kinds may be used as the surfactants.

The first organic material may be a nitrogen- or sulfur-containing organic compound. For example, the sulfur-containing organic material may include a linear or branched hydrocarbon compound having a thiol group at one end. In a specific example, the sulfur-containing organic compound may be one or more selected from among HS—$C_n$—$CH_3$ (n: an integer ranging from 2 to 20), n-dodecyl mercaptan, methyl mercaptan, ethyl mercaptan, butyl mercaptan, ethylhexyl mercaptan, isooctyl mercaptan, tert-dodecyl mercaptan, thioglycolacetic acid, mercaptopropionic acid, mercaptoethanol, mercaptopropanol, mercaptobutanol, mercaptohexanol and octyl thioglycolate.

The second organic material may be a phase-transfer catalyst-based organic compound, for example, quaternary ammonium or a phosphonium salt. More specifically, the second organic surfactant may be one or more selected from among tetraocylyammonium bromide, tetraethylammonium, tetra-n-butylammonium bromide, tetramethylammonium chloride, and tetrabutylammonium fluoride.

Figure 3D:
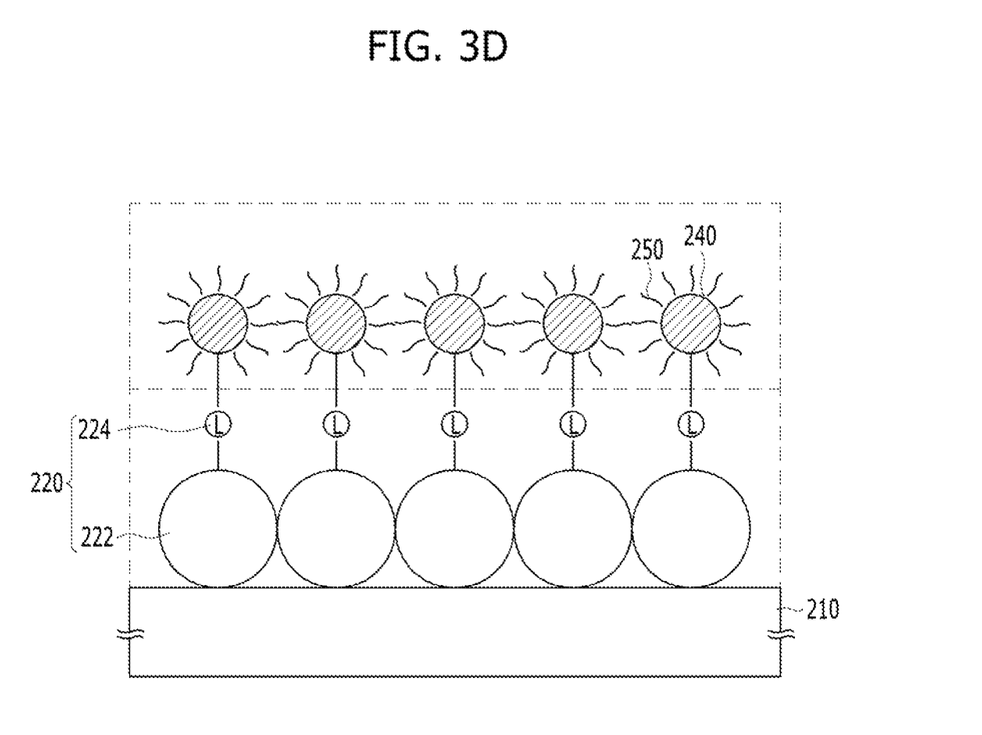

FIG. 3D shows metallic nanoparticles 240 with the receptors 250 bonded thereto. The receptors 250 may be bonded to or coat the surfaces of the metallic nanoparticles 240. All materials suitable for being bonded to the surface of the metallic nanoparticles 240 and suitable for reacting with a marker may be used as the receptors 250.

The marker may be a protein, a nucleic acid, an oligosaccharide, an amino acid, carbohydrates, a solution gas, a sulfur oxide gas, a nitrogen oxide gas, pesticide residue, a heavy metal, or an environmentally harmful substance. The receptors 250 may be at least one selected from an enzyme substrate, a ligand, an amino acid, a peptide, a protein, a nucleic acid, a lipid, and carbohydrates. The receptors 250 may be bonded to or coat the surfaces of the grown metallic nanoparticles 240 through functional groups. The functional groups of the receptors 250 may be at least one selected from an amine group, a carboxylic acid group, and a thiol group.

Referring to FIG. 3D, the sensor platform formed through the fabrication method in accordance with the second embodiment is described in detail.

The sensor in accordance with the second embodiment includes a nanostructure for physical, electrical, chemical, and optical sensing of a marker.

The nanostructure may include dielectric material particle supporters 222 formed over the substrate 210 and linkers 224 bonded thereto, and metallic nanoparticles 240 that are grown from metal ions bonded to the linkers 224. Also, the nanostructure may further include receptors 250 bonded to the surface of the metallic nanoparticles 240.

The substrate 210 may include a surface layer 214 having functional groups suitable for bonding to the linkers 224. The surface layer may include an oxide layer. To be specific, non-limiting examples of the surface layer of the substrate 210 may be a layer of at least one material selected from a silicon oxide, a hafnium oxide, an aluminum oxide, a zirconium oxide, a barium-titanium composite oxide, an yttrium oxide, a tungsten oxide, a tantalum oxide, a zinc oxide, a titanium oxide, a tin oxide, a barium-zirconium composite oxide, a silicon nitride, a silicon oxynitride, a zirconium silicate, and a hafnium silicate.

The substrate 210 may be a flexible substrate, which may include a surface layer 214 of an organic substance having a hydroxyl (—OH) functional groups that suitable for being bonded to the linkers 224. The flexible substrate may include one or a mixture of two or more selected from polyethylene terephthalate (PET), polyethylene naphthalate (PEN), polyimide (PI), polycarbonate (PC), polypropylene (PP), triacetyl cellulose (TAC), polyethersulfone (PES), and polydimethylsiloxane (PDMS).

The dielectric material particle supporter 222 may be an oxide particle having at least one element selected from metals, transition metals, post-transition metals, and metalloids. The dielectric material particle supporter 222 may be a particle having a particle diameter of about 10 to 20 nm. The dielectric material particle supporter 222 may be formed in a single layer or in multiple layers (a layer multiple dielectric particle supporters thick).

Also, the dielectric material particle supporter 222 may include at least one material selected from a silicon oxide, a hafnium oxide, an aluminum oxide, a zirconium oxide, a barium-titanium composite oxide, an yttrium oxide, a tungsten oxide, a tantalum oxide, a zinc oxide, a titanium oxide, a tin oxide, a barium-zirconium composite oxide, a silicon nitride, a silicon oxynitride, a zirconium silicate, a hafnium silicate and polymers.

The linkers 224 may be organic molecules. The nanostructure may include a linker layer formed of the linkers 224 bonded to the surface of the substrate 210. The linker layer may be a self-assembled monomolecular layer on the surface of the dielectric material particle supporters 222. The linkers 224 may include one functional group selected from an amine group, a carboxylic acid group, and a thiol group. Each of the linkers 120A may include a first functional group bonded to the surface of the dielectric material particle supporters 222, a second functional group bonded to metal ions, and a chain group for connecting the first functional group and the second functional group to each other.

The metallic nanoparticles 240 may be selected from metal nanoparticles, metal oxide nanoparticles, metal nitride nanoparticles, metal carbide nanoparticles, and intermetallic compound nanoparticles. The metallic nanoparticles 240 are grown by bonding metal ions to the linkers 224 and then growing the metal ions.

The size of the metallic nanoparticles 240 may be controlled according to the energy application conditions while the metallic nanoparticles 240 are grown. Also, the size of nanoparticles may be controlled before the energy for growing the metallic nanoparticles 240 is applied or while applying the energy by whether a surfactant is supplied. The surfactant may be an organic surfactant, and the surfactant may remain on the surface of the metallic nanoparticles 240 after the growing of the metallic nanoparticles 240 is finished. According to an embodiment, when no surfactant is used, the metallic nanoparticles 240 may have a particle diameter of about 2.0 to 3.0 nm.

According to another embodiment, when a single surfactant is used, the metallic nanoparticles 240 may have a particle diameter of about 1.3 to 1.6 nm. According to another embodiment, when multiple kinds of surfactant are used, the metallic nanoparticles 240 may have a particle diameter of about 0.5 to 1.2 nm. Embodiments of the metallic nanoparticles 240 may be the same as or similar to those of the above-described first embodiment.

The receptors 250 may be bonded to or coat the surface of the grown metallic nanoparticles 240. All materials suitable for reacting with a marker (which is a target material), such as a protein, a nucleic acid, an oligosaccharide, an amino acid, carbohydrates, a solution gas, a sulfur oxide gas, a nitrogen oxide gas, a pesticide residue, a heavy metal, or an environmentally harmful substance, may be used as the receptors 250. The receptors 250 may be at least one selected from an enzyme substrate, a ligand, an amino acid, a peptide, a protein, a nucleic acid, a lipid, and carbohydrates. The receptors 250 may include at least one functional group selected from an amine group, a carboxylic acid group, and a thiol group. The functional group allows the receptors 250 to be bonded to the surface of the metallic nanoparticles 240.

According to an embodiment, a sensor platform may be formed of high-density nanoparticles that are extremely fine and uniform in size. Even when scaled down, the sensor platform has excellent operation stability, reproducibility, and reliability. Also, since the nanoparticles are fixed by dielectric linkers, physical stability is excellent as well.

A method according to an embodiment may allow direct fabrication of a nanostructure through a simple process of forming a metal ion layer by using linkers and applying energy to the metal ion layer while fabricating the sensor. Therefore, mass-production may be realized through a simple process at a low cost. Also, since the nanostructure platform is fabricated in-situ, waste of raw materials may be minimized.

Although various embodiments have been described for illustrative purposes, it will be apparent to those skilled in the art that various changes and modifications may be made without departing from the spirit and scope of the disclosure as defined in the following claims.

What is claimed is:

1. A sensor, comprising:
 a nanostructure as a sensing element for sensing a marker over a substrate,
 wherein the nanostructure comprises:
 a linker layer, including linkers, bonded to the substrate;
 metallic nanoparticles formed over the linker layer and grown from metal ions which are bonded to the linkers over the substrate; and
 an organic surfactant of one or more kinds bonded to a surface of the metal ions or the metallic nanoparticles, wherein the organic surfactant controls size of the metallic nanoparticles.

2. The sensor of claim 1, further comprising:
 receptors bonded to a surface of the metallic nanoparticles.

3. The sensor of claim 2, wherein the receptors include one or more selected from a group comprising an enzyme substrate, a ligand, an amino acid, a peptide, a protein, a nucleic acid, a lipid, and carbohydrates.

4. The sensor of claim 1, wherein the substrate includes a surface layer where the linkers are bonded.

5. The sensor of claim 1, wherein the metallic nanoparticles have an average particle diameter of about 0.5 nm to 3.0 nm.

6. The sensor of claim 1, wherein the linkers include a functional group, selected from a group comprising an amine group, a carboxyl group, and a thiol group.

7. The sensor of claim 1, wherein the linker layer includes a self-assembled monomolecular layer or a silane compound layer.

8. The sensor of claim 1, wherein the metallic nanoparticles are arranged separately from each other to form a single layer of the metallic nanoparticles.

9. The sensor of claim 1, wherein the nanostructure has a vertical multi-stack structure where the linker layer and a nanoparticle layer, which is formed of the metallic nanoparticles, are stacked alternately and repeatedly.

10. A sensor, comprising:
 a nanostructure as a sensing element for sensing a marker over a substrate,
 wherein the nanostructure comprises:
 dielectric material particle supporters formed over the substrate;
 linkers bonded to a surface of the dielectric material particle supporters;
 metallic nanoparticles grown from metal ions which are bonded to the linkers over the substrate; and
 an organic surfactant of one or more kinds bonded to a surface of the metal ions or the metallic nanoparticles, wherein the organic surfactant controls size of the nanoparticles.

11. The sensor of claim 10, further comprising:
 receptors bonded to a surface of the metallic nanoparticles.

12. The sensor of claim 11, wherein the receptors include one or more selected from a group comprising an enzyme substrate, a ligand, an amino acid, a peptide, a protein, a nucleic acid, a lipid, and carbohydrates.

13. The sensor of claim 10, wherein the dielectric material particle supporters with the linkers bonded thereto are arranged over the substrate to form a single supporter layer or a vertically stacked multi-layer structure.

14. The sensor of claim 10, wherein the linkers include one or more functional groups selected from a group comprising an amine group, a carboxyl group, and a thiol group, that are suitable for bonding to the metal ions.

15. The sensor of claim 10, wherein the nanostructure further comprises:
   an organic surfactant of one or more kinds bonded to surfaces of the metal ions or the nanoparticles.

16. The sensor of claim 10, wherein the metallic nanoparticles have an average particle diameter of about 0.5 nm to 3.0 nm.

17. A method for fabricating a sensor, comprising:
   forming a linker layer including linkers over a substrate;
   bonding metal ions to the linkers of the linker layer;
   forming metallic nanoparticles over the linker layer by growing the metal ions which are bonded to the linkers over the substrate;
   bonding an organic surfactant of one or more kinds to a surface of the metal ions or the metallic nanoparticles, wherein the organic surfactant controls size of the metallic nanoparticles; and
   bonding receptors to a surface of the metallic nanoparticles.

18. The method of claim 17, wherein the metal ions are aggregated by application of energy.

19. The method of claim 18, further comprising:
   supplying the organic surfactant of one or more kinds before or during the application of the energy.

20. The method of claim 17, wherein the linker layer is formed by applying a linker solution, where the linkers are dissolved in a solvent, to a surface of the substrate.

21. The method of claim 17, wherein the linker layer is formed through an Atomic Layer Deposition (ALD) method using a gas containing the linkers.

22. The method of claim 17, wherein the linkers have a functional group that is bonded to the metal ions.

23. The method of claim 17, wherein the bonding of the metal ions to the linkers of the linker layer includes:
   applying a metal precursor to the linkers.

24. The method of claim 23, wherein the bonding of the metal ions to the linkers of the linker layer further includes:
   applying a metal precursor solution, where the metal precursor is dissolved, to the linkers, or
   applying a metal precursor gas to the linkers.

25. The method of claim 18, wherein the energy is at least one selected from a group comprising heat energy, chemical energy, light energy, vibration energy, ion beam energy, electron beam energy, and radiation energy.

26. The method of claim 18, wherein an additional substance is applied to the metallic nanoparticles or the metallic ions, resulting in part or all of the metallic nanoparticles being comprised of a material that is different than what would have been achieved without the application of the additional substance.

27. A method for fabricating a sensor, comprising:
   forming a linker layer including linkers over a substrate;
   forming dielectric material particle supporters over a substrate and bonding the linkers to the dielectric material particle supporters;
   bonding metal ions to the linkers;
   forming metallic nanoparticles over the linker layer by growing the metal ions which are bonded to the linkers over the substrate;
   bonding an organic surfactant of one or more kinds to a surface of the metal ions or the metallic nanoparticles, wherein the organic surfactant controls size of the metallic nanoparticles; and
   bonding receptors to a surface of the metallic nanoparticles.

28. The method of claim 27, wherein the metal ions are aggregated by application of energy.

29. The method of claim 28, further comprising:
   supplying the organic surfactant of one or more kinds before or during the application of the energy.

30. The method of claim 27, wherein the forming of the dielectric material particle supporters with the linkers bonded thereto includes:
   preparing a supporter material by mixing dielectric material particle supporters and linkers in a solvent to form a solution; and
   coating the substrate with the supporter material or depositing the supporter material on the substrate.

31. The method of claim 27, wherein the bonding of the metal ions to the linkers includes:
   applying a metal precursor to the linkers.

32. The method of claim 31, wherein the bonding of the metal ions to the linkers further includes:
   applying a metal precursor solution, where the metal precursor is dissolved, to the linkers, or
   applying a metal precursor gas to the linkers.

33. The method of claim 28, wherein the energy is one or more selected from a group comprising heat energy, chemical energy, light energy, vibration energy, ion beam energy, electron beam energy, and radiation energy.

34. The method of claim 28, wherein an additional substance is applied to the metallic nanoparticles or the metallic ions before or during the application of energy, resulting in part or all of the metallic nanoparticles being comprised of a material that is different than what would have been achieved without the application of the additional substance.

* * * * *